United States Patent [19]

Bruns et al.

[11] Patent Number: 4,992,416

[45] Date of Patent: Feb. 12, 1991

[54] ISOMERIC FORMYL TRIMETHYLBICYCLO[2.2.2]OCT-7-ENES

[75] Inventors: Klaus Bruns, Krefeld-Traar; Thomas Gerke, Neuss, both of Fed. Rep. of Germany; Michael Virnig, Santa Rosa, Calif.

[73] Assignee: Henkel Kommanditgesellschaft auf Aktien, Duesseldorf, Fed. Rep. of Germany

[21] Appl. No.: 348,353

[22] Filed: May 5, 1989

[30] Foreign Application Priority Data

May 5, 1988 [DE] Fed. Rep. of Germany ....... 3815259

[51] Int. Cl.$^5$ .................. A61K 7/46; C07C 47/44
[52] U.S. Cl. ........................ 512/16; 424/70; 512/8; 512/14; 568/445
[58] Field of Search .............. 424/70; 512/8, 16, 14; 568/445, 446

[56] References Cited

U.S. PATENT DOCUMENTS 3,914,322 10/1975 Chappell et al. ................. 260/617

FOREIGN PATENT DOCUMENTS 143252 1/1931 Switzerland ................. 568/445
611517 6/1979 Switzerland ................. 512/16

OTHER PUBLICATIONS

Chem. Abstr., 76, 4021z, (1972); Houben-Weyl, Bd. V/1c, pp. 977-1139, (1966).
Chemical Abstract, 97:163242x, 1982.
Chemical Abstract, 109:128453m, 1988.

Primary Examiner—Werren B. Lone
Attorney, Agent, or Firm—Ernest G. Szoke; Wayne C. Jaeschke; Henry E. Millson, Jr.

[57] ABSTRACT

Isomeric formyl trimethylbicyclo[2.2.2]oct-7-enes, their use as perfumes, and a process for their preparation comprising a Diels-Alder reaction of acrolein with either 1,5,5-trimethylcyclohexa-1,3-diene, 3,5,5-trimethylcyclohexa-1,3-diene, 5,5-dimethyl-3-methylenecyclohex-1-ene or mixtures thereof.

17 Claims, No Drawings

ISOMERIC FORMYL TRIMETHYLBICYCLO[2.2.2]OCT-7-ENES

BACKGROUND OF THE INVENTION

1. Field of the Invention:

This invention relates to isomeric formyl trimethylbicyclo[2.2.2]oct-7-enes, to their production, and to their use as perfumes.

2. Statement of Related Art:

Bicyclo[2.2.2]octenes are already known as perfumes from the literature. For example, bicyclooctenes substituted by an isopropyl group are described in Chem. Abstr. 76,4021z (1972). Substituted tetramethylbicyclo[2.2.2]octenes are disclosed in CH 611 517.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that isomeric formyl trimethylbicyclo[2.2.2]oct-7-enes have surprising and valuable properties as perfumes.

Accordingly, the present invention relates to isomeric formyl trimethylbicyclo[2.2.2]oct-7-enes corresponding to the following general formulae

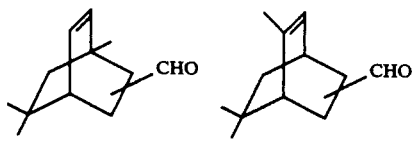

The present invention also relates to the use of these isomeric formyl trimethylbicyclo[2.2.2]oct-7-enes as perfumes, and to compositions containing them.

The odor of the isomer mixtures of the invention can be described as green and herb-like with a grass and hay note. The mixtures of the invention are also characterized by extremely high odor stability.

The isomeric formyl trimethylbicyclo[2.2.2]oct-7-enes of the invention are useful for the production of new, interesting perfume compositions where fresh, herb-like perfume notes are desired. Based on the composition as a whole, the content of the isomeric formyl trimethylbicyclo[2.2.2]oct-7enes is between 1 and 50% by weight and preferably between 1 and 25% by weight. These compositions can be used for the perfuming of commercial products, such as detergents and disinfectants, fabric treatment preparations, cosmetics of all kinds, such as toilet waters, creams, lotions, aerosols, toilet soaps, make-up and lipsticks and also in extract perfumery. The content of the perfume compositions of the invention in the perfumed products is between 2 and 20% by weight and preferably between 5 and 10% by weight.

The isomeric formyl trimethylbicyclo[2.2.2]oct-7-enes are prepared by a Diels-Alder reaction (see Wollweber in Houben-Weyl, Vol. V/1c, pages 977-1139 (1970)). To this end, 1,5,5-trimethylcyclohexa-1,3-diene, 3,5,5-trimethylcyclohexa-1,3-diene, 5,5-dimethyl-3-methylene-cyclohex-1-ene or mixtures containing one or more of these dienes are reacted with acrolein at a temperature in the range of from 20° to 220° C., optionally in the presence of catalysts The molar ratio of diene to acrolein is between 0.5:1 and 2:1 and preferably between 0.6:1 and 1.5:1. The catalysts include, for example, $BF_3$, $AlCl_3$ and/or $ZnCl_2$. The reaction is preferably carried out in an organic solvent, such as methylene chloride, dimethyl ether, and/or cyclohexane. On completion of the reaction, the isomeric product is isolated from the reaction mixture Preferably, the reaction product is washed with water, neutralized, for example with aqueous sodium hydrogen carbonate solution, aqueous sodium carbonate solution and/or potassium hydroxide, and then distilled.

The dienes to be used as educts for the preparation of the bicyclooctenes of the invention can be prepared by standard known methods of organic chemistry, for example by reduction of 3,5,5-trimethylcyclohex-2-en-1-one (isophorone) with, for example, lithium aluminum hydride to the corresponding alcohol 3,5,5-trimethylcyclohexen-1-ol. This alcohol is then reacted, for example, with potassium hydrogen sulfate to form dienes which can be used in accordance with the invention as educts for the production of isomeric formyl trimethylbicyclo[2.2.2]oct-7-enes.

The invention will be illustrated but not limited by the following examples.

EXAMPLES

1. Reduction of isophorone to 3,5,5-trimethylcyclohexen-1-ol 200 g isophorone (1.45 mol) in 500 ml absolute dimethyl ether were added dropwise with stirring to 13.77 g lithium aluminum hydride (0.3625 mol, suspended in 200 ml absolute dimethyl ether) in such a way that continuous refluxing occurred. The reaction mixture was thereafter refluxed for 1 hour. For working up, first ice water and then 10% sulfuric acid were carefully added with stirring after cooling, followed by separation in a separation funnel and extraction three times with ether.

After the organic phase had been washed with saturated sodium chloride solution, the organic phase was concentrated and distilled in a water jet vacuum (16 torr) at 60°-62° C. Yield: 170 g (84% of the theoretical)

2. Preparation of the diene mixture 170 g 3,5,5-trimethyl cyclohexen-1-ol obtained by reduction of isophorone in step 1 above, and 10 g potassium hydrogen sulfate were heated under nitrogen to the boiling temperature, the diene mixture distilling off. After drying with sodium sulfate, the diene mixture was directly used in the Diels Alder reaction in step 3 below

3. Preparation of 5(6)-formyl-1,3,3(3,3,7)-trimethyl-bicyclo[2.2.2]oct-7ene by Diels-Alder reaction 122 g (1 mol) of the diene mixture obtained in accordance with step 2 above containing 1,5,5-trimethylcyclohexa-1,3-diene,-3,5,5-trimethylcyclohexa-1,3-diene and 5,5-dimethyl-3-methylene-cyclohex-1-ene in a ratio by weight of 55:25:20, 84 g acrolein, and 6.11 g zinc chloride were dissolved in 200 ml methylene chloride and boiled under reflux for 4 hours For working up, the reaction product was washed with 100 ml water, neutralized with 100 ml of an aqueous saturated sodium hydrogen carbonate solution, and purified by distillation after removal of the solvent.

Isomeric 5(6)-1,3,3(3,3,7)-trimethylbicyclo[2.2.2]oct-7-ene boiling at 58° C. to 60° C./0.08 mbar was obtained in a yield of 115 g=65% of the theoretical.

COMPOSITION EXAMPLES

Fancy lavender

|  | Parts by weight |
| --- | --- |
| 5(6)-formyl-1,3,3(3,3,7)-trimethyl bicyclo[2.2.2]oct-7-ene | 400 |
| Lavandin oil Gross | 200 |
| α-Terpineol | 100 |
| Linalyl acetate | 100 |
| Linalool | 50 |
| Musk ketone | 40 |
| Lavender oil, French | 30 |
| Coumarin | 20 |
| Sandalwood oil (Haarmann & Reimer) | 20 |
| Patchouli oil | 20 |
| Camphor | 15 |
| Ambroxan (Henkel), 10% by weight in isopropyl myristate | 5 |
|  | 1000 |
| Formulation for a foam bath/shampoo |  |
| 5(6)-formyl-1,3,3(3,3,7)-trimethyl bicyclo[2.2.2]oct-7-ene | 200 |
| Pine needle oil, Sibir. | 100 |
| Isobornyl acetate | 80 |
| α-Amyl cinnamaldehyde | 80 |
| Phenyl ethyl alcohol | 70 |
| Lavandin oil Grosso | 70 |
| p-Tert.-butyl cyclohexyl acetate | 60 |
| Nopyl acetate | 50 |
| Orange oil sweet | 50 |
| Cyclovertal (Henkel) 10% by weight in dipropylene glycol | 40 |
| Cedryl acetate | 40 |
| Galaxolide (IFF) | 40 |
| Geraniol | 30 |
| Geranyl nitrile | 30 |
| Styarallyl acetate | 20 |
| Galbanum Resin synth. (RBD) | 20 |
| Phenyl acetaldehyde dimethyl acetal | 10 |
| Cylcohexyl salicylate (Henkel) | 10 |
|  | 1000 |

We claim:

1. Isomeric formyl trimethylbicyclo[2.2.2]oct-7-enes of the formulae

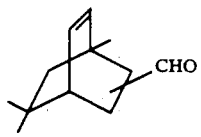 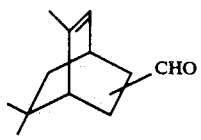

2. Isomeric 5(6)-formyl-1,3,3(3,3,7)-trimethylbicyclo[2.2.2]oct-7-ene.

3. A process for the production of isomeric formyl trimethylbicyclo[2.2.2]oct-7-enes of the formula

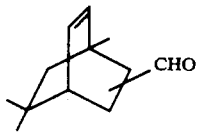 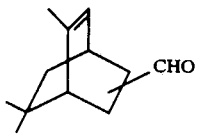

comprising the steps of A. reacting either 1,5,5-trimethylcyclohexa-1,3-diene, 3,5,5-trimethylcyclohexa-1,3-diene, 5,5-dimethyl-3-methylene cyclohex-1-ene or a mixture thereof with acrolein at a temperature in the range of from about 20° to about 220° C., wherein the molar ratio of diene to acrolein is between about 0.5:1 and 2:1, and B. and isolating the isomeric formyl trimethylbicyclo[2.2.2]oct-7enes from the resulting reaction mixture.

4. The process of claim 3 wherein in step A the molar ratio of diene to acrolein is from about 0.6:1 to about 1.5:1.

5. The process of claim 3 wherein step A is carried out in the presence of a catalyst.

6. The process of claim 5 wherein the catalyst is BF$_3$, AlCl$_3$, ZnCl$_2$, or a mixture of the two or more of the foregoing.

7. The process of claim 4 wherein the catalyst is BF$_3$, AlCl$_3$, ZnCl$_2$, or a mixture of two or more of the foregoing.

8. The process of claim 3 wherein step A is carried out in an organic solvent.

9. The process of claim 8 wherein the organic solvent is methylene chloride, dimethyl ether, cyclohexane, or a mixture of the two or more of the foregoing.

10. The process of claim 3 wherein step B is carried out by first washing the reaction mixture from step A with water, neutralizing the reaction mixture, and distilling the reaction mixture.

11. The process of claim 3 wherein in step A the molar ratio of diene to acrolein is from about 0.6:1 to about 1.5:1, and the reaction is carried out in the presence of a catalyst and an organic solvent.

12. A method of imparting a perfume fragrance to a substrate comprising applying to the substrate a fragrance-enhancing quantity of at least one isomeric formyl trimethylbicyclo[2.2.2.]oct-7-ene of the formulae

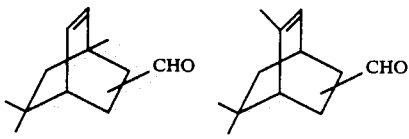

13. The method of claim 12 wherein the substrate is a detergent composition, a disinfectant composition, a fabric treatment preparation, a cosmetic composition, or a perfume composition.

14. In a perfume composition, the improvement comprising the presence therein of a fragrance-enhancing quantity of at least one isomeric formyl trimethylbicyclo[2.2.2]oct-7-ene of the formulae

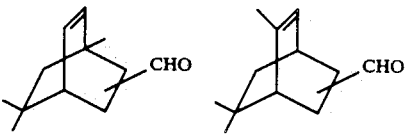

15. The perfume composition of claim 14 wherein at least one isomeric formyl trimethylbicyclo[2.2.2]oct-7-ene is present in from about 1 to about 50% by weight of the perfume composition.

16. The perfume composition of claim 15 wherein from about 1 to about 25% by weight of at least one isomer is present therein.

17. In a detergent composition, a disinfectant composition, a fabric treatment preparation, or a cosmetic composition, the improvement comprising the presence therein of from about 2 to about 20% by weight of the perfume composition of claim 15.

* * * * *